(12) United States Patent
Jones et al.

US011586106B2

(10) Patent No.: US 11,586,106 B2
(45) Date of Patent: Feb. 21, 2023

(54) IMAGING APPARATUS HAVING CONFIGURABLE STEREOSCOPIC PERSPECTIVE

(71) Applicant: Titan Medical Inc., Toronto (CA)

(72) Inventors: Evan Rittenhouse Jones, Levittown, NY (US); Maxime Blain, Rosedale, NY (US); Christopher Dean Smith, Shirley, NY (US)

(73) Assignee: TITAN MEDICAL INC., Toronto (CA)

( * ) Notice: Subject to any disclaimer, the term of this patent is extended or adjusted under 35 U.S.C. 154(b) by 568 days.

(21) Appl. No.: 16/235,246

(22) Filed: Dec. 28, 2018

(65) Prior Publication Data

US 2020/0209730 A1    Jul. 2, 2020

(51) Int. Cl.
| | | |
|---|---|---|
| *A61B 1/00* | (2006.01) | |
| *A61B 34/30* | (2016.01) | |
| *G03B 35/04* | (2021.01) | |
| *H04N 13/296* | (2018.01) | |
| *H04N 13/239* | (2018.01) | |
| *G02B 26/08* | (2006.01) | |
| *G02B 3/12* | (2006.01) | |
| *G02B 5/06* | (2006.01) | |
| *H04N 13/00* | (2018.01) | |

(52) U.S. Cl.
CPC ........... *G03B 35/04* (2013.01); *A61B 1/0019* (2013.01); *A61B 1/00096* (2013.01); *A61B 1/00193* (2013.01); *A61B 34/30* (2016.02); *H04N 13/239* (2018.05); *H04N 13/296* (2018.05); *A61B 2034/302* (2016.02); *G02B 3/12* (2013.01); *G02B 5/06* (2013.01); *G02B 26/0816* (2013.01); *G02B 26/0875* (2013.01); *G02B 26/0883* (2013.01); *H04N 2013/0081* (2013.01); *H04N 2213/001* (2013.01)

(58) Field of Classification Search
CPC ....................... A61B 1/00193; A61B 1/00183
See application file for complete search history.

(56) References Cited

U.S. PATENT DOCUMENTS

| 6,132,368 A | 10/2000 | Cooper |
|---|---|---|
| 6,206,903 B1 | 3/2001 | Ramans |

(Continued)

*Primary Examiner* — Alexandra L Newton
(74) *Attorney, Agent, or Firm* — Carter, DeLuca & Farrell, LLP (57) ABSTRACT

In some embodiments, a stereoscopic imaging apparatus includes a tubular housing having a bore extending longitudinally through the housing. First and second image sensors are disposed proximate a distal end of the bore, each including a light sensitive elements on a face and mounted facing laterally outward. The apparatus further includes a first beam steering element associated with the first image sensor and a second beam steering element associated with the second image sensor. The beam steering elements receive light from first and second perspective viewpoints and direct the received light onto the faces of the image sensors forming first and second images. Either the first and second beam steering elements or the first and second image sensors are moveable to cause a change a spacing between or an orientation of the perspective viewpoints to cause sufficient disparity between the first and second images to provide image data including three-dimensional information.

14 Claims, 4 Drawing Sheets

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,414,779 B1 * | 7/2002 | Mandella ............ A61B 1/00183 359/201.1 |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |

(56) References Cited

U.S. PATENT DOCUMENTS

| | | |
|---|---|---|
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,271,637 B2 | 3/2016 | Farr |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 2014/0092215 A1* | 4/2014 | Hayama ............ A61B 1/00045 348/45 |
| 2014/0210945 A1* | 7/2014 | Morizumi ............ A61B 1/05 348/45 |

* cited by examiner

IMAGING APPARATUS HAVING CONFIGURABLE STEREOSCOPIC PERSPECTIVE

BACKGROUND

1. Field

This disclosure relates generally to stereoscopic imaging and more particularly to a stereoscopic imaging apparatus wherein a spacing between or an orientation of the stereoscopic viewpoints may be changed to cause sufficient disparity between images for generating three-dimensional (3D) information.

2. Description of Related Art

Stereoscopic imaging generally involves capturing a pair of images from spaced apart perspective viewpoints and processing the images to generate a three-dimensional (3D) view or 3D information based on a disparity between the images. Small format image sensors may be used to generate stereoscopic images while being sufficiently small to fit within a small diameter tubular housing. However when the spacing between image sensors is constrained by the size of the housing, the disparity between images may be insufficient particularly when viewing images that are close to the image sensors. The lack of disparity results in some views providing an inadequate 3D viewing effect. The extraction of 3D information may also be limited by the lack of disparity between stereo images.

SUMMARY

In accordance with some embodiments there is provided a stereoscopic imaging apparatus. The apparatus includes a tubular housing configured for insertion into a confined space, the tubular housing having a bore extending longitudinally through the housing. The apparatus also includes first and second image sensors disposed proximate a distal end of the bore, each image sensor including a plurality of light sensitive elements on a face of the image sensor and being mounted facing laterally outward with respect to a longitudinal axis extending through the bore. The apparatus further includes a first beam steering element associated with the first image sensor and a second beam steering element associated with the second image sensor, the beam steering elements being operably configured to receive light from respective first and second perspective viewpoints extending longitudinally outward into an object field and direct the received light onto the faces of the respective first and second image sensors for forming respective first and second images. Either the first and second beam steering elements or the first and second image sensors are moveable to cause a change at least one of a spacing between and an orientation of the perspective viewpoints with respect to a longitudinal axis of the bore to cause sufficient disparity between the first and second images to provide image data including three-dimensional information.

Each of the first and second beam steering elements may include a plurality of beam steering elements disposed in different locations with respect to the longitudinal axis and the first and second image sensors may be moveable to cause the first and second images to be selectively received by one of the plurality of beam steering elements.

The first and second image sensors may be mounted back-to-back on a moveable carrier.

The moveable carrier may include a circuit substrate.

The moveable carrier may be constrained for longitudinal motion within the bore and may further include an actuator disposed within the bore and operably configured to cause longitudinal movement of the carrier.

The actuator may include one of a piezoelectric actuator, a rotary piezoelectric motor, and a control wire.

The plurality of beam steering elements may be disposed in different locations may include longitudinally spaced apart prisms at a periphery of the housing, each prism being operably configured to receive light from a different perspective viewpoint.

Each of the first and second beam steering elements may include a moveable reflective element operably configured to be pivoted to receive light from different perspective viewpoints.

The moveable reflective elements are operably configured to be disposed along an outer periphery of the housing while the apparatus is being inserted into the confined space and are deployable after insertion to receive light from the respective first and second perspective viewpoints.

Each of the first and second beam steering elements may include a deformable optical element operably configured to deform to receive light from different perspective viewpoints.

The deformable optical element may include at least one of a liquid lens and a liquid prism.

The apparatus may include an actuator operably configured to cause movement of imaging lenses associated with each of the first and second image sensors in a direction aligned with the longitudinal axis to cause a change in orientation of the perspective viewpoints with respect to a longitudinal axis.

The tubular housing may be attached to a distal end of an elongate sheath having a passage extending through the sheath for carrying signals to and from the image sensors.

At least a portion of the sheath may include a manipulator operably configured to cause the sheath to be bend for positioning the tubular housing with the confined space.

The confined space may include a body cavity of a patient undergoing a medical or surgical procedure.

The stereoscopic imaging apparatus may be used in a robotic surgery system.

The tubular housing may have a generally circular cross section.

The bore of the tubular housing may have a diameter of about 10 millimeters.

The apparatus may include a controller in communication with the apparatus and operably configured to cause movement of either the first and second beam steering elements or the first and second image sensors in response to making a determination that an object field being captured by the apparatus may have insufficient disparity between the first and second images to provide image data including three-dimensional information.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
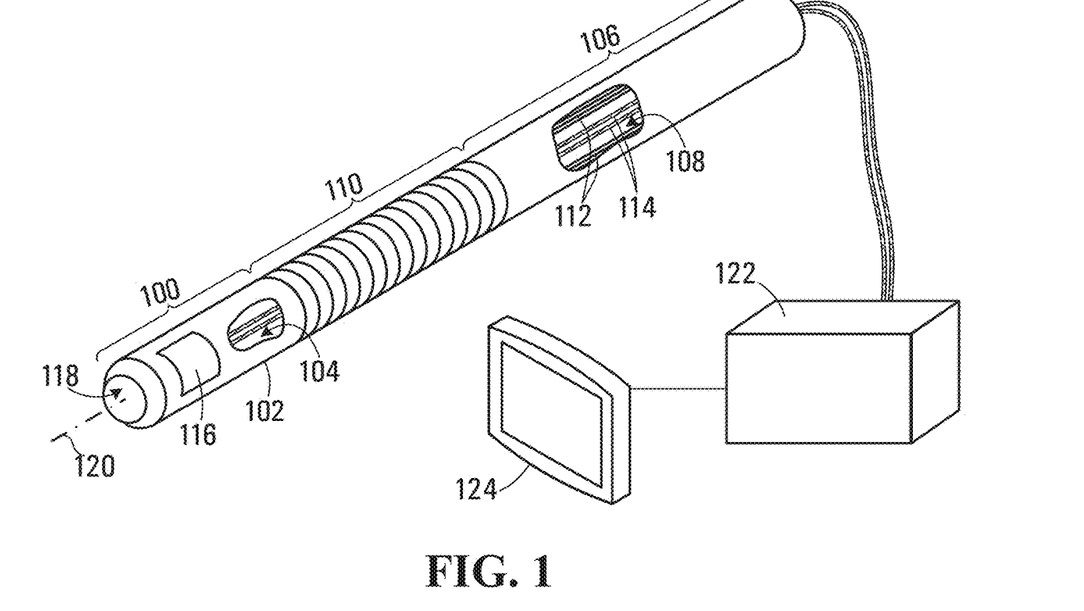
FIG. 1 is a perspective view of a stereoscopic imaging apparatus.

Referring to FIG. 1, a stereoscopic imaging apparatus in accordance with a first embodiment is shown generally at 100. The apparatus 100 includes a tubular housing 102 configured for insertion into a confined space. The tubular housing 102 has a bore 104 extending longitudinally through the housing that accommodates imaging components (shown in FIG. 2). In the embodiment shown, the tubular housing 102 has a generally circular cross section, which in one embodiment may have a diameter of about 10 millimeters.

In the embodiment shown, the tubular housing is attached to a distal end of an elongate sheath 106 having a passage 108 extending through the sheath for carrying signals to and from the imaging components within the tubular housing 102. A portion of the sheath 106 includes a manipulator 110, which is configured to cause the sheath to be bent to position the tubular housing within the confined space for capturing images. In one embodiment, the manipulator may include a plurality of vertebra actuated to bend by a plurality of control links or cables 112 for disposing the apparatus 100 at various positions with respect to a longitudinal axis 120 of the bore 104. The passage 108 also accommodates various signal cables 114 for carrying image data to a host system controller 122 and for transmitting control and command signals to the apparatus 100. The host system controller 122 is in communication with a display 124 for displaying the images, which may be viewed through a stereoscopic viewing device (not shown) to provide separate left and right stereoscopic images to a user's left and right eyes.

The apparatus 100 includes a first beam steering element 116 laterally disposed on the tubular housing 102 of the apparatus 100 proximate a distal end 118. A second beam steering element (not visible in FIG. 1) is similarly laterally disposed on the opposite side of the tubular housing 102. The beam steering element 116 in FIG. 1 is shown schematically as a demarcated portion of the tubular housing 102 but may take on various forms, such as described in more detail below.

In one embodiment, the confined space within which the apparatus 100 may be employed may be a body cavity of a patient undergoing a medical or surgical procedure. For example, the apparatus 100 may be used for imaging during a laparoscopic surgery procedure or may be part of a robotic surgery system for performing robotic surgery.

Figure 2:
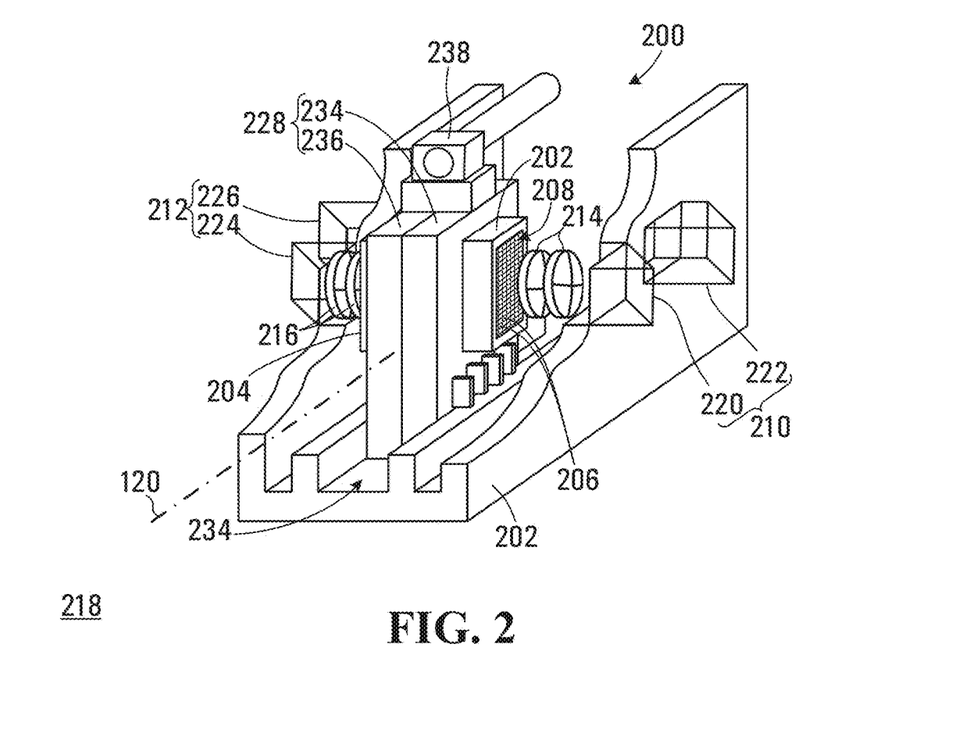
FIG. 2 is a perspective view of an imaging assembly of the stereoscopic imaging apparatus shown in FIG. 1.

Referring to FIG. 2, the apparatus 100 includes an imaging assembly shown generally at 200. The imaging assembly 200 includes a first image sensor 202 and a second image sensor 204 (of which only a portion is visible in FIG. 2). The first and second image sensors 202 and 204 are substantially identical and are disposed proximate the distal end 118 of the bore 104 mounted facing laterally outward with respect to the longitudinal axis 120 of the bore. Each of the image sensors 202 and 204 include a plurality of light sensitive elements 206 on a face 208 of the image sensor.

The imaging assembly 200 also includes a first beam steering element 210 associated with the first image sensor 202 and a second beam steering element 212 associated with the second image sensor 204. The beam steering element 210 is operably configured to receive light from a first perspective viewpoint in an object field 218, which is directed through an imaging lens 214 onto the face 208 of the image sensor 202 for forming a first image. The beam steering element 212 is operably configured to receive light from a second perspective viewpoint in the object field 218, which is directed through an imaging lens 216 onto the face of the image sensor 204 for forming a second image.

In this embodiment, the first beam steering element 210 includes two prisms 220 and 222 longitudinally spaced apart at a periphery of the imaging assembly 200. Similarly, the second beam steering element 212 includes two prisms 224 and 226 longitudinally spaced apart on an opposite side of the imaging assembly 200. The first and second image sensors 202 and 204 are moveable along the longitudinal axis 120 to cause the first and second images to be selectively received by either the prisms 220, 224 or the prisms 222, 226. In the embodiment shown in FIG. 2, the first and second image sensors 202 and 204 are mounted back-to-back on a moveable carrier 228, which in the embodiment shown comprises respective circuit substrates 234 and 236 on which the imaging sensors are mounted. In the embodiment shown in FIG. 1 the imaging lenses 214 and 216 are each mounted in a lens tube (shown in FIG. 3) which is coupled to the respective first and second image sensors 202 and 204 and thus move with the sensors and the moveable carrier 228.

The moveable carrier 228 is received within a channel 230 in a frame 232 (shown partially cut-away in FIG. 2 to reveal underlying elements). The frame 232 is received within and fixed relative to the bore 104 of the tubular housing 102. The moveable carrier 228 is constrained for longitudinal movement within the channel 230 of the frame 232 in a direction aligned with the longitudinal axis 120 of the bore. The imaging assembly 200 further includes an actuator 238 which is coupled to the moveable carrier 228 to cause the longitudinal movement on the carrier when actuated by a control signal provided by the host system controller 122. In some embodiments the actuator 238 may be a piezoelectric actuator, a rotary piezoelectric motor, or a control wire, for example.

In the imaging assembly 200 shown in FIG. 2, the moveable carrier 228 is disposed such that the first and second image sensors 202 and 204 receive images via the prisms 220 and 224 respectively. The optical configuration corresponding to FIG. 2 is shown in plan view in FIG. 3A, in which the first and second image sensors 202 and 204 have perspective viewpoints 300 and 302 within the object field 218. The perspective viewpoints 300 and 302 are separated by a distance $D_1$ and in this embodiment where the prisms 220 and 224 have a 45° prism angle, the perspective viewpoints are also substantially parallel.

Figure 3A:
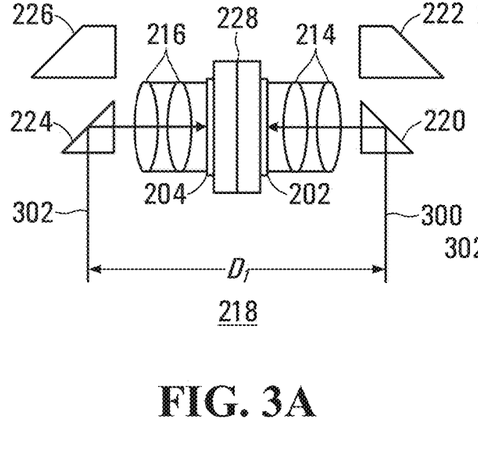
FIG. 3A is a schematic plan view of an optical configuration of the imaging apparatus shown in FIG. 2.
Figure 3B:
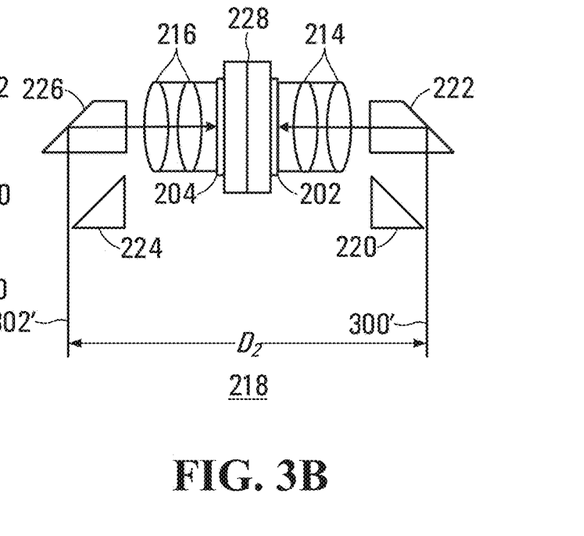
FIG. 3B is a schematic plan view of a further optical configuration of the imaging apparatus shown in FIG. 2 and FIG. 3A.

Referring to FIG. 3B, when the moveable carrier 228 is moved by the actuator 238 to align the sensors 202 and 204 with the prisms 222 and 226, the first and second image sensors have respective perspective viewpoints 300' and 302' within the object field 218. The perspective viewpoints 300' and 302' are separated by a distance $D_2$ and due to the 45° prism angle of the prisms 222 and 226, are also substantially parallel. The increased separation between the perspective viewpoints from $D_1$ to $D_2$ increases the disparity between the first and second images received at the respective first and second image sensors 202 and 204. The increased image disparity may provide for more effective display and extraction of 3D information. Under some imaging conditions the smaller disparity $D_1$ as shown in FIG. 3A may be insufficient to provide a view having appreciable 3D depth.

Figure 4:
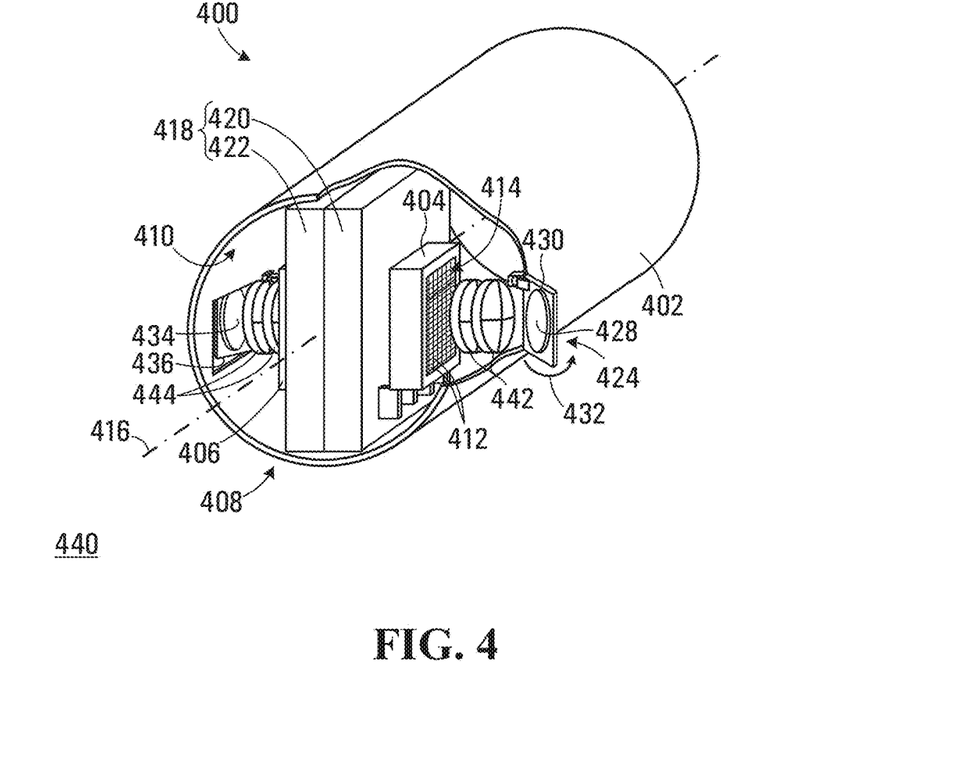
FIG. 4 is a perspective view of a stereoscopic imaging apparatus in accordance with another embodiment.

Referring to FIG. 4, a stereoscopic imaging apparatus in accordance with another embodiment is shown generally at 400. The apparatus 400 includes a tubular housing 402, shown partially cut away in FIG. 4 to reveal imaging components. The apparatus 400 includes first and second image sensors 404 and 406 disposed back-to-back and proximate a distal end 408 of a bore 410. The back-to-back mounting has an advantage of providing options for packaging the optical components within the tubular housing 102 in that the image sensors 404 and 406 may be located proximate a widest portion of the bore 104. In systems where image sensors are disposed side-by-side at a distal end of a tubular housing and facing the object field 218, the maximum size of sensor that can be accommodated would have a width of less than half of the diameter of the tubular housing 102. For a 10 millimeter diameter housing, the maximum diagonal size of image sensor would be about 6 millimeters (or ¼ inch). The configuration of imaging assembly 200 shown in FIG. 2 would permit the sensors to be increased in size to close to the full 10 millimeters (or just less than ½ inch). While image sensors as small as 3.62 millimeters (⅐ inch) are now available, a larger image sensor may provide improved light capture, imaging performance, reduced image signal noise, and also increased image resolution.

The image sensors 404 and 406 each include a plurality of light sensitive elements 412 on a face 414 of the image sensors. The image sensors 404 and 406 are mounted on a carrier 418 facing laterally outward with respect to a longitudinal axis 416 extending through the bore 410. In this embodiment the carrier 418 is made up by circuit substrates 420 and 422 on which the sensors 404 and 406 are mounted. In this embodiment the carrier 418 and image sensors 404 and 406 are immobilized within the bore 410 of the tubular housing 402.

The apparatus 400 also includes a first beam steering element 424 associated with the first image sensor 404 and a second beam steering element 426 associated with the second image sensor 406. The first beam steering element 424 in this embodiment is implemented using a reflective element or mirror 428 mounted on a moveable support 430 via hinges to the tubular housing 102 and operable to pivot outwardly as indicated by the arrow 432. Similarly, the second beam steering element 426 includes a mirror 434 mounted on a moveable support 436 mounted via hinges to the tubular housing 102 and operable to pivot outwardly. In this embodiment the first beam steering element 424 includes a miniature actuator 438 coupled to the moveable support 430 to cause the movement 432 for deploying the mirror. The second beam steering element 426 also includes an actuator (not visible in FIG. 4) for actuating movement of the moveable support 436. While the apparatus 100 is being inserted into a confined space, the beam steering elements 424 and 426 may be maintained in an un-deployed disposition lying along an outer periphery of the housing 102. Once the apparatus 100 is inserted, the beam steering elements 424 and 426 may be deployed to receive light from an object field 440. The mirrors 428 and 434 each receive light from different perspective viewpoints within the object field 440. The received light is directed by the respective mirrors 428 and 434 through lenses 442 and 444 toward the sensors 404 and 406 for forming left and right images on the sensors.

Figure 5A:
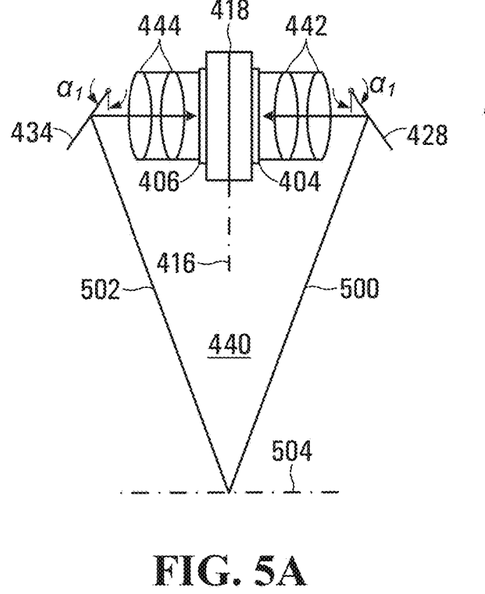
FIG. 5A is a schematic plan view of an optical configuration of the imaging apparatus shown in FIG. 4.

Referring to FIG. 5A, the apparatus 400 is shown in a first deployed operating condition where the mirrors 428 and 434 are pivoted outwardly to an angle $\alpha_1$ of about 35° with respect to the longitudinal axis 416. Under these conditions the image sensors 404 and 406 receive light from respective first and second perspective viewpoints 500 and 502 that are angled inwardly (or toed in) toward the longitudinal axis 416 and converge at a convergence plane 504. Images captured of objects located at the convergence plane 504 will not have any disparity and will appear to be located at a screen plane when viewed on the display 124 using a 3D viewing device. Objects closer to the apparatus 400 than the convergence plane 504 will exhibit positive parallax and will appear to be located rearwardly of the screen plane, while objects behind the convergence plane 504 will have negative parallax and appear to be located forward of the screen plane.

Figure 5B:
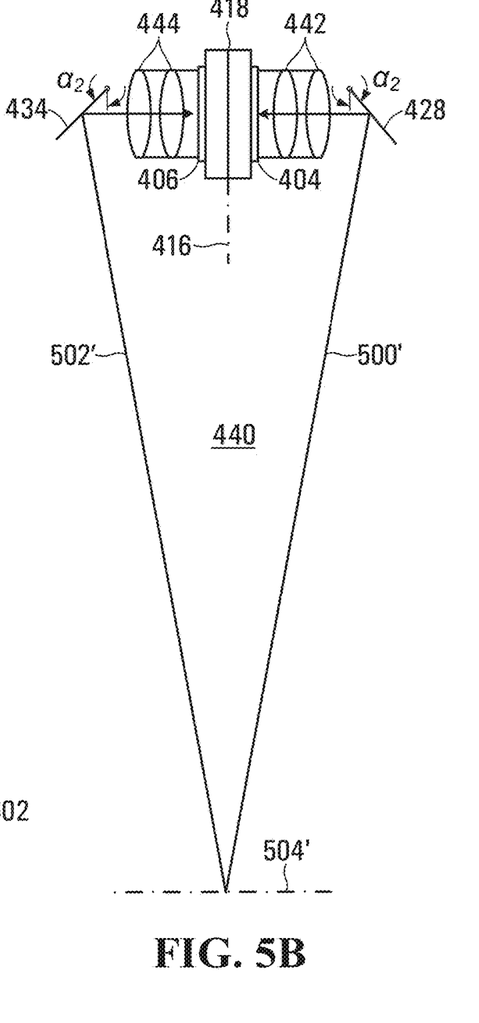
FIG. 5B is a schematic plan view of a further optical configuration of the imaging apparatus shown in FIG. 4 and FIG. 5A.

In FIG. 5B, the mirrors 428 and 434 are pivoted outwardly to an angle $\alpha_2$ of about 40° such that the image sensors 404 and 406 receive light from respective first and second perspective viewpoints 500' and 502' that are less inwardly angled with respect to the longitudinal axis 416. This has the effect of moving an associated convergence plane 504' for the perspective viewpoints 506 and 508 outwardly with respect to the apparatus 400.

One advantage of the configuration shown in FIGS. 5A and 5B is that the convergence plane 504 may be located at a desired depth in the object field 440 to facilitate generation of 3D information at the desired depth. Some 3D information may also generated for objects located away from the convergence plane 504, but the 3D effects are enhanced and the resulting view may result in increased eyestrain for the user.

Referring back to FIG. 2, FIG. 3A and FIG. 3B, in the embodiment shown the prisms 220 and 224 may be configured with a prism angle less than 45° to cause the perspective viewpoints 300 and 302 to be angled inwardly, generally as shown in FIG. 5. The prisms 222 and 226 may be configured with a prism angle less than 45° to cause the perspective viewpoints 300' and 302' to be angled inwardly. Other embodiments may be configured to maintain the parallel perspective viewpoints 300' and 302', while the perspective viewpoints 300 and 302 are toed in. Parallel perspective viewpoints effectively locate the convergence plane at infinity such that the screen plane is at infinity and all objects are displayed having positive parallax.

Figure 6:
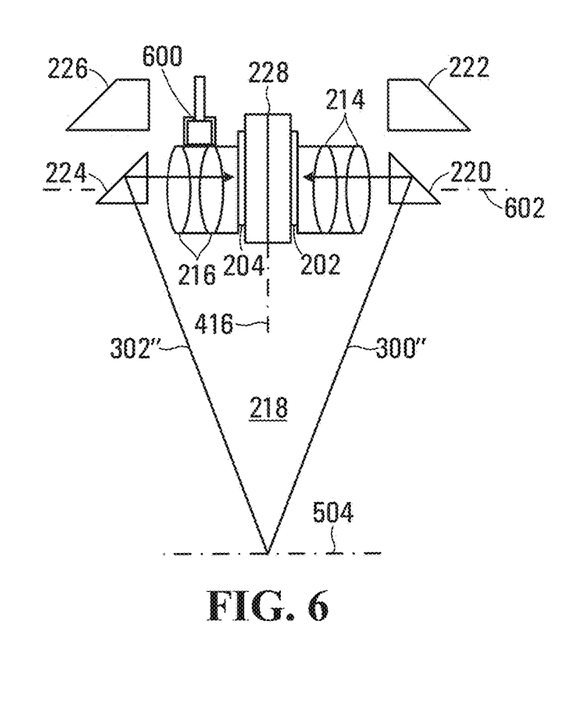
FIG. 6 is a schematic plan view of an optical configuration for implementing some embodiments.

In an embodiment configured as shown in FIG. 3A and FIG. 3B, the prism angle once selected remains fixed. Referring to FIG. 6, in some embodiments the imaging assembly 200 may further include an actuator 600 and the imaging lenses 214 and 216 may be moveable in a direction aligned with the longitudinal axis 416 in response to movement of the actuator. Displacement of the imaging lenses 214 and 216 with respect to an optical centerline 602 of the first and second image sensors 202 and 204 causes the perspective viewpoints 300" and 302" to be toed in to a degree permitted by the optical design of the imaging lenses.

In some embodiments one or more conventional optical elements of the imaging assembly 200 or apparatus 400 may be replaced with a deformable optical element. For example the prisms 220-226 may be implemented as a liquid prism that is capable of changing beam steering characteristics in response to a control signal received from the host system controller 122. Similarly, one or more of the imaging lenses 214 216, 442, or 444 may include a deformable optical element such as a liquid lens. The deformable optical element facilitates some adjustment of the perspective viewpoint orientation and/or separation by changing optical properties of the deformable element.

In some embodiments the host system controller 122 may be configured to make a determination whether the object field 218 or object field 440 being captured by the imaging assembly 200 or imaging apparatus 400 is capable of providing sufficient disparity between the first and second images for successful extraction of 3D information. The host system controller 122 may be further configured to cause movement of the applicable first beam steering elements, imaging lenses, or deformable optics when insufficient disparity is found in the images currently being captured.

Figure 7A:
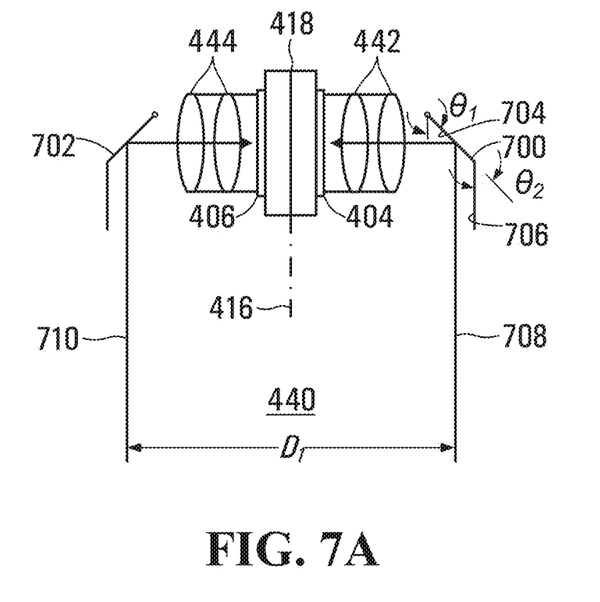
FIG. 7A is a schematic plan view of another optical configuration of the imaging apparatus shown in FIG. 4 in accordance with another embodiment.

In some embodiments the mirrors 428 and 434 (shown in FIGS. 4 and 5) may be replaced by mirrors 700 and 702 as shown in FIG. 7A. Each of the mirrors 700 and 702 in FIG. 7A has a first reflective surface 704 and a second reflective surface 706. The first reflective surface 704 is disposed at an angle $\theta_1$, which in the example shown is 45° resulting in perspective viewpoints 708 and 710 within the object field 440 generally as described in connection with FIG. 3A. The perspective viewpoints 708 and 710 are separated by a distance $D_1$ and in this embodiment where the first reflective surface 704 is at a 45° angle to the longitudinal axis 416 are also substantially parallel.

Figure 7B:
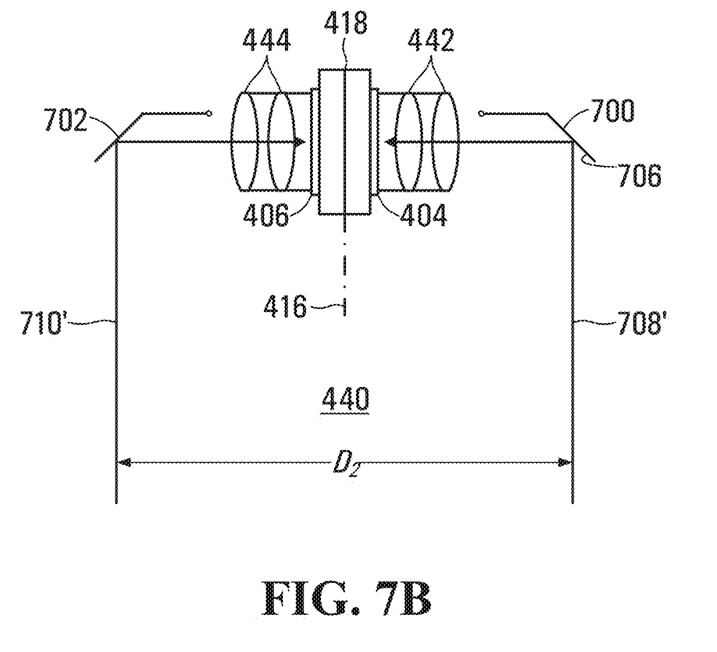
FIG. 7B is a schematic plan view of the optical configuration of the imaging apparatus shown in FIG. 7A.

Referring to FIG. 7B, when the mirrors 700 and 702 are pivoted further outwardly with respect to the longitudinal axis 416, the first and second image sensors 404 and 406 will have respective perspective viewpoints 708' and 710' within the object field 440. The perspective viewpoints 708' and 710' are separated by a distance $D_2$ and due to the further 45° angle of the second reflective surface 706, are also substantially parallel. In this embodiment the mirrors 700 and 702 may also be actuated to angles other than 45°, thus facilitating toeing in the perspective viewpoints while also providing a selectable spacing between the perspective viewpoints.

The embodiments set forth above provide for selectively changing orientation and/or the spacing between perspective viewpoints for producing stereoscopic views of an object field. The back-to-back orientation of the lateral facing image sensors also facilitates the accommodation of the imaging components within a small bore housing suitable for insertion into confined spaces. The provision of beam steering elements that are located peripherally on the housing increases the spacing between perspective viewpoints over a side-by-side image sensor configuration.

While specific embodiments have been described and illustrated, such embodiments should be considered illustrative only and not as limiting the disclosed embodiments as construed in accordance with the accompanying claims.

What is claimed is:

1. A stereoscopic imaging apparatus comprising:
   a tubular housing configured to be inserted into a confined space, the tubular housing including a bore extending longitudinally through the tubular housing;
   first and second image sensors disposed proximate a distal end of the bore, each image sensor including a plurality of light sensitive elements on a face of the image sensor and being mounted facing laterally outward with respect to a longitudinal axis extending through the bore;
   a first beam steering element associated with the first image sensor and a second beam steering element associated with the second image sensor, the first and second beam steering elements configured to receive light from respective first and second perspective viewpoints extending longitudinally outward into an object field and direct the received light onto the faces of the respective first and second image sensors to form respective first and second images; and
   a first movable support mounted via a first hinge to the tubular housing and fixedly supporting the first beam steering element thereon, and a second movable support mounted via a second hinge to the tubular housing and fixedly supporting the second beam steering element thereon,
   wherein the first and second beam steering elements are pivotably moveable outside the tubular housing to cause a change in an orientation of the perspective viewpoints with respect to the longitudinal axis of the bore to cause sufficient disparity between the first and second images to provide image data including three-dimensional (3D) information.

2. The apparatus of claim 1, wherein each of the first and second beam steering elements comprises a moveable reflective element configured to be pivoted to receive light from different perspective viewpoints.

3. The apparatus of claim 2, wherein the moveable reflective elements are configured to be disposed along an outer periphery of the tubular housing while the apparatus is being inserted into the confined space and are deployable after insertion to receive light from the respective first and second perspective viewpoints.

4. The apparatus of claim 1 wherein each of the first and second beam steering elements comprises a deformable optical element configured to deform to receive light from different perspective viewpoints.

5. The apparatus of claim 4 wherein the deformable optical element comprises at least one of a liquid lens or a liquid prism.

6. The apparatus of claim 1 further comprising an actuator configured to cause movement of imaging lenses associated with each of the first and second image sensors in a direction aligned with the longitudinal axis to cause a change in orientation of the perspective viewpoints with respect to a longitudinal axis.

7. The apparatus of claim 1, wherein the tubular housing is attached to a distal end of an elongate sheath having a passage extending through the elongate sheath to carry signals to and from the first and second image sensors.

8. The apparatus of claim 7, wherein at least a portion of the elongate sheath comprises a manipulator configured to cause the elongate sheath to be bent to position the tubular housing with the confined space.

9. The apparatus of claim 1, wherein the confined space comprises a body cavity of a patient undergoing a medical or surgical procedure.

10. The apparatus of claim 9, wherein the stereoscopic imaging apparatus is used in a robotic surgery system.

11. The apparatus of claim 1, wherein the tubular housing includes a generally circular cross section.

12. The apparatus of claim 1, wherein the bore of the tubular housing has a diameter of about 10 millimeters.

13. The apparatus of claim 1, further comprising a controller in communication with the apparatus and configured to cause movement of either the first and second beam steering elements or the first and second image sensors based on a determination of whether or not the object field being captured by the apparatus provides sufficient disparity between the first and second images to extract three-dimensional (3D) information.

14. A stereoscopic imaging apparatus comprising:
first and second image sensors configured to be disposed proximate a distal end of a bore of a tubular housing, each image sensor including a plurality of light sensitive elements on a face of the image sensor and being mounted facing laterally outward with respect to a longitudinal axis extending through the bore of the tubular housing;
a first beam steering element associated with the first image sensor and a second beam steering element associated with the second image sensor, the first and second beam steering elements configured to receive light from respective first and second perspective viewpoints extending longitudinally outward into an object field and direct the received light onto the faces of the respective first and second image sensors to form respective first and second images ; and
a first movable support mounted via a first hinge to the tubular housing and fixedly supporting the first beam steering element thereon, and a second movable support mounted via a second hinge to the tubular housing and fixedly supporting the second beam steering element thereon,
wherein the first and second beam steering elements are pivotably moveable outside the tubular housing to cause a change in an orientation of the perspective viewpoints with respect to the longitudinal axis of the bore of the tubular housing to cause sufficient disparity between the first and second images to provide image data including three-dimensional (3D) information.

* * * * *